(12) United States Patent
Matsumoto et al.

(10) Patent No.: US 10,416,004 B2
(45) Date of Patent: Sep. 17, 2019

(54) RESIN IMPREGNATION DETECTION DEVICE, COIL FOR ROTATING MACHINE, AND METHOD FOR IMPREGNATING AND MOLDING RESIN OF COIL FOR ROTATING MACHINE

(71) Applicant: MITSUBISHI ELECTRIC CORPORATION, Chiyoda-ku (JP)

(72) Inventors: Michihito Matsumoto, Chiyoda-ku (JP); Kazushi Sekine, Chiyoda-ku (JP); Ichiya Takahashi, Chiyoda-ku (JP)

(73) Assignee: MITSUBISHI ELECTRIC CORPORATION, Chiyoda-ku (JP)

( * ) Notice: Subject to any disclaimer, the term of this patent is extended or adjusted under 35 U.S.C. 154(b) by 0 days.

(21) Appl. No.: 16/086,832

(22) PCT Filed: Feb. 7, 2017

(86) PCT No.: PCT/JP2017/005920
§ 371 (c)(1),
(2) Date: Sep. 20, 2018

(87) PCT Pub. No.: WO2017/191705
PCT Pub. Date: Nov. 9, 2017

(65) Prior Publication Data
US 2019/0113369 A1    Apr. 18, 2019

(30) Foreign Application Priority Data

May 2, 2016    (JP) .................................. 2016-092340

(51) Int. Cl.
*G01D 5/353* (2006.01)
*G01F 23/00* (2006.01)
(Continued)

(52) U.S. Cl.
CPC ......... *G01D 5/353* (2013.01); *G01D 5/35316* (2013.01); *G01D 5/35377* (2013.01);
(Continued)

(58) Field of Classification Search
None
See application file for complete search history.

(56) References Cited

U.S. PATENT DOCUMENTS

| 5,142,151 A | * | 8/1992 | Varnell | ................ G01N 21/314 |
| | | | | 250/339.08 |
| 5,519,211 A | * | 5/1996 | Bur | ..................... B29C 35/0288 |
| | | | | 250/227.19 |

(Continued)

FOREIGN PATENT DOCUMENTS

| JP | 11-94688 A | | 4/1999 |
| JP | 2005156831 A | * | 6/2005 |
| JP | 2014035312 A | * | 2/2014 |

OTHER PUBLICATIONS

International Search Report dated Apr. 18, 2017, in PCT/JP2017/005920 filed Feb. 17, 2017.

*Primary Examiner* — Rhonda S Peace
(74) *Attorney, Agent, or Firm* — Oblon, McClelland, Maier & Neustadt, L.L.P.

(57) ABSTRACT

A resin impregnation detection device configured to detect resin impregnation in a resin impregnation process for a coil insulation layer. The resin impregnation detection device can be inserted in a narrow portion, is capable of detecting impregnation with a liquid resin, and does not leave metal foreign materials other than an optical fiber in a product even after the resin impregnation. The resin impregnation detection device includes an optical fiber including an FBG sensor, and a coating resin, which coats the FBG sensor. The coating resin includes a resin to be softened by contact with a detection target resin. The FBG sensor is applied with a (Continued)

compressive strain caused by cure shrinkage of the coating resin or heat shrinkage thereof from a curing temperature to a normal temperature.

15 Claims, 19 Drawing Sheets

(51) Int. Cl.
- *G01N 21/41* (2006.01)
- *G02B 6/00* (2006.01)
- *G02B 6/02* (2006.01)
- *G01L 1/24* (2006.01)
- *H01F 5/06* (2006.01)
- *H01F 27/40* (2006.01)
- *H01F 41/12* (2006.01)
- *H02K 3/30* (2006.01)
- *G01N 21/77* (2006.01)
- *H02K 15/12* (2006.01)

(52) U.S. Cl.
CPC .............. *G01F 23/00* (2013.01); *G01L 1/246* (2013.01); *G01N 21/41* (2013.01); *G01N 21/7743* (2013.01); *G02B 6/00* (2013.01); *G02B 6/02* (2013.01); *H01F 5/06* (2013.01); *H01F 27/402* (2013.01); *H01F 41/127* (2013.01); *H02K 3/30* (2013.01); *H02K 15/12* (2013.01)

(56) References Cited

U.S. PATENT DOCUMENTS

| | | | | |
|---|---|---|---|---|
| 5,770,155 | A * | 6/1998 | Dunphy | B29C 35/0288 250/227.14 |
| 7,672,544 | B2 * | 3/2010 | Takabayashi | B60K 15/077 385/12 |
| 8,076,909 | B2 * | 12/2011 | Diatzikis | H02K 11/25 322/99 |
| 8,285,086 | B2 * | 10/2012 | Nishikawa | G01N 21/774 385/12 |
| 8,351,029 | B2 * | 1/2013 | Nishikawa | G01D 5/35383 356/128 |
| 8,520,986 | B2 * | 8/2013 | Dailey | G01D 5/35303 250/227.11 |
| 10,161,810 | B2 * | 12/2018 | Sekine | G01D 5/35316 |
| 2005/0082467 | A1 * | 4/2005 | Mossman | G01B 11/16 250/227.16 |
| 2007/0116402 | A1 * | 5/2007 | Slade | G01N 21/7703 385/12 |
| 2013/0048841 | A1 * | 2/2013 | Hunt | G01M 11/086 250/227.14 |
| 2014/0327335 | A1 * | 11/2014 | Mabuchi | H01F 5/06 310/208 |
| 2015/0098819 | A1 * | 4/2015 | Tourin | G01M 5/0033 416/1 |
| 2015/0225563 | A1 * | 8/2015 | Yamamoto | H02K 3/30 310/208 |
| 2016/0084733 | A1 * | 3/2016 | Wu | G01B 11/18 250/227.14 |
| 2017/0248460 | A1 * | 8/2017 | Staudinger | G01F 23/22 |
| 2018/0266947 | A1 * | 9/2018 | Coonrod | G01D 5/35316 |
| 2019/0113369 | A1 * | 4/2019 | Matsumoto | G01D 5/353 |

* cited by examiner

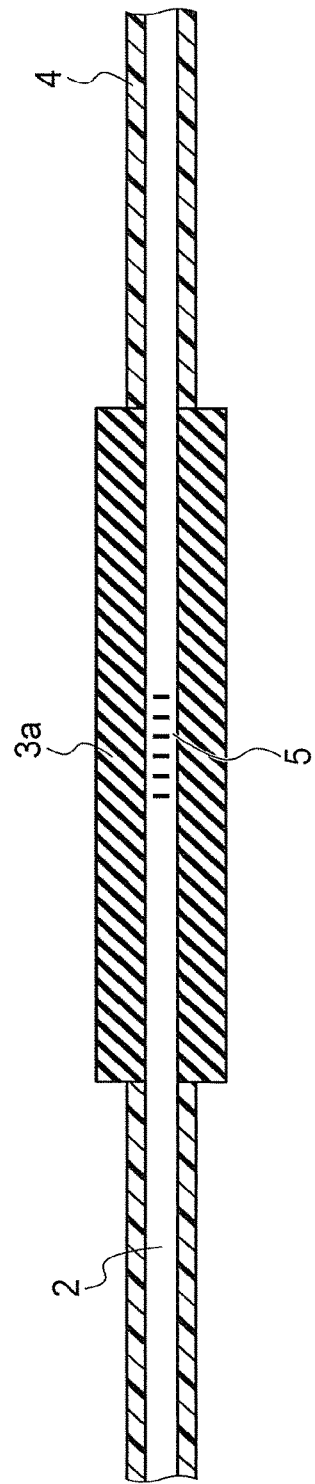
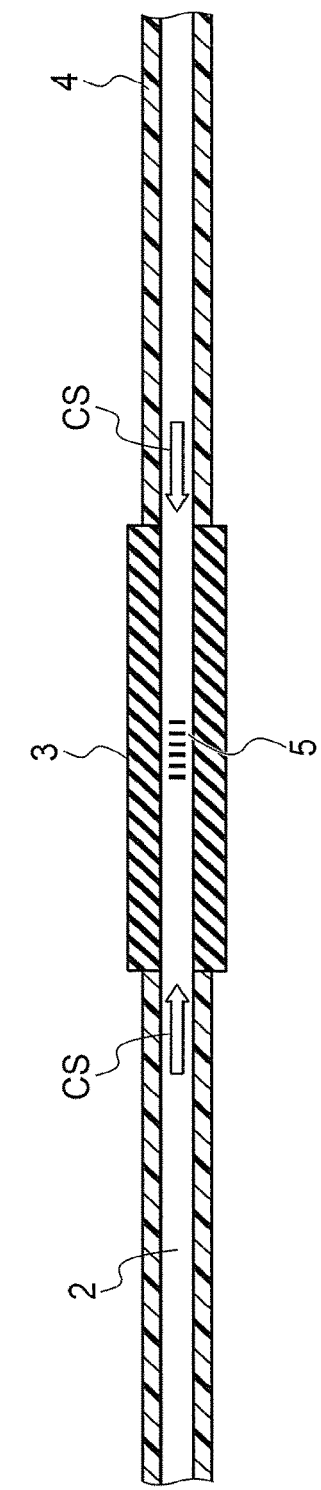

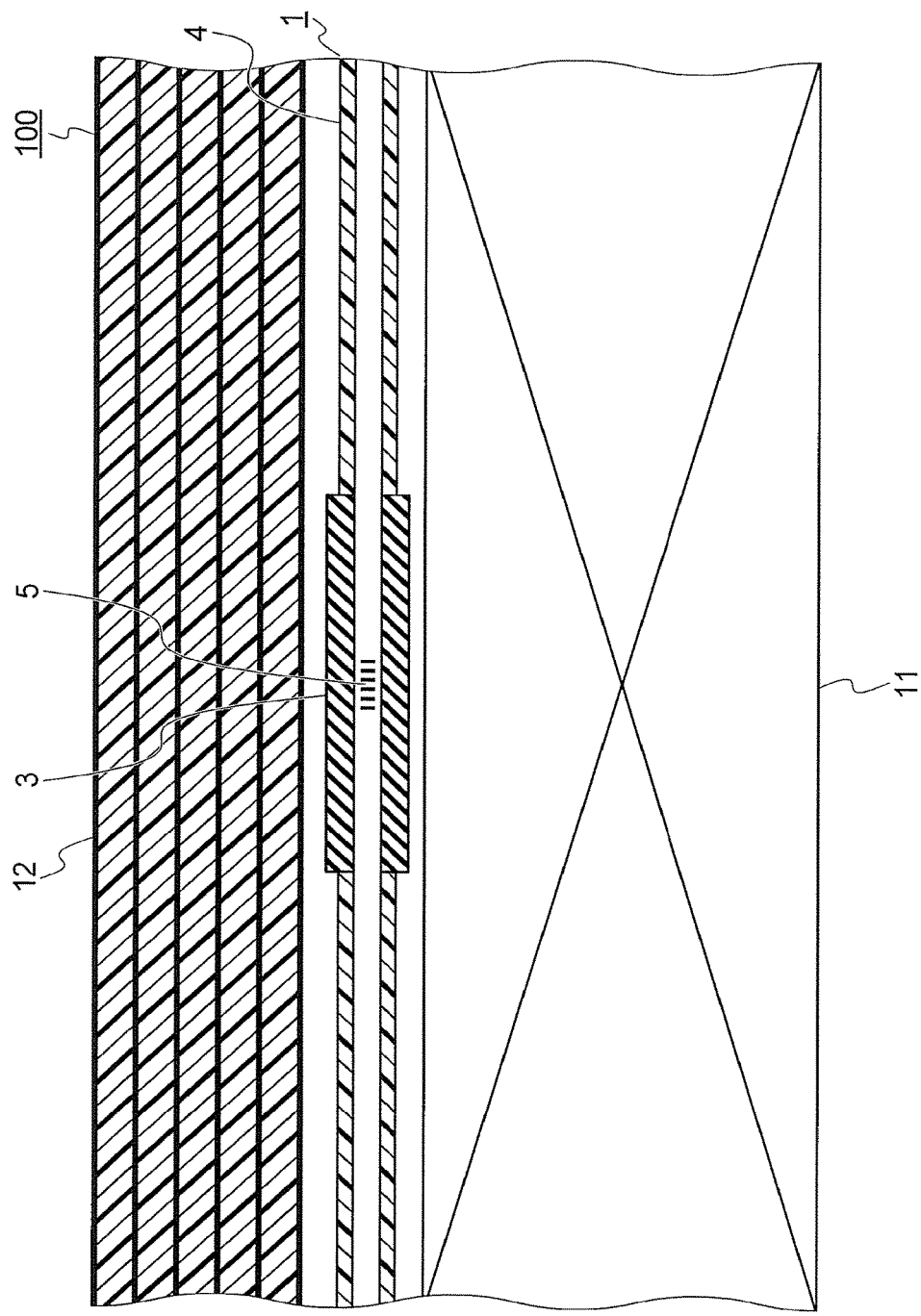

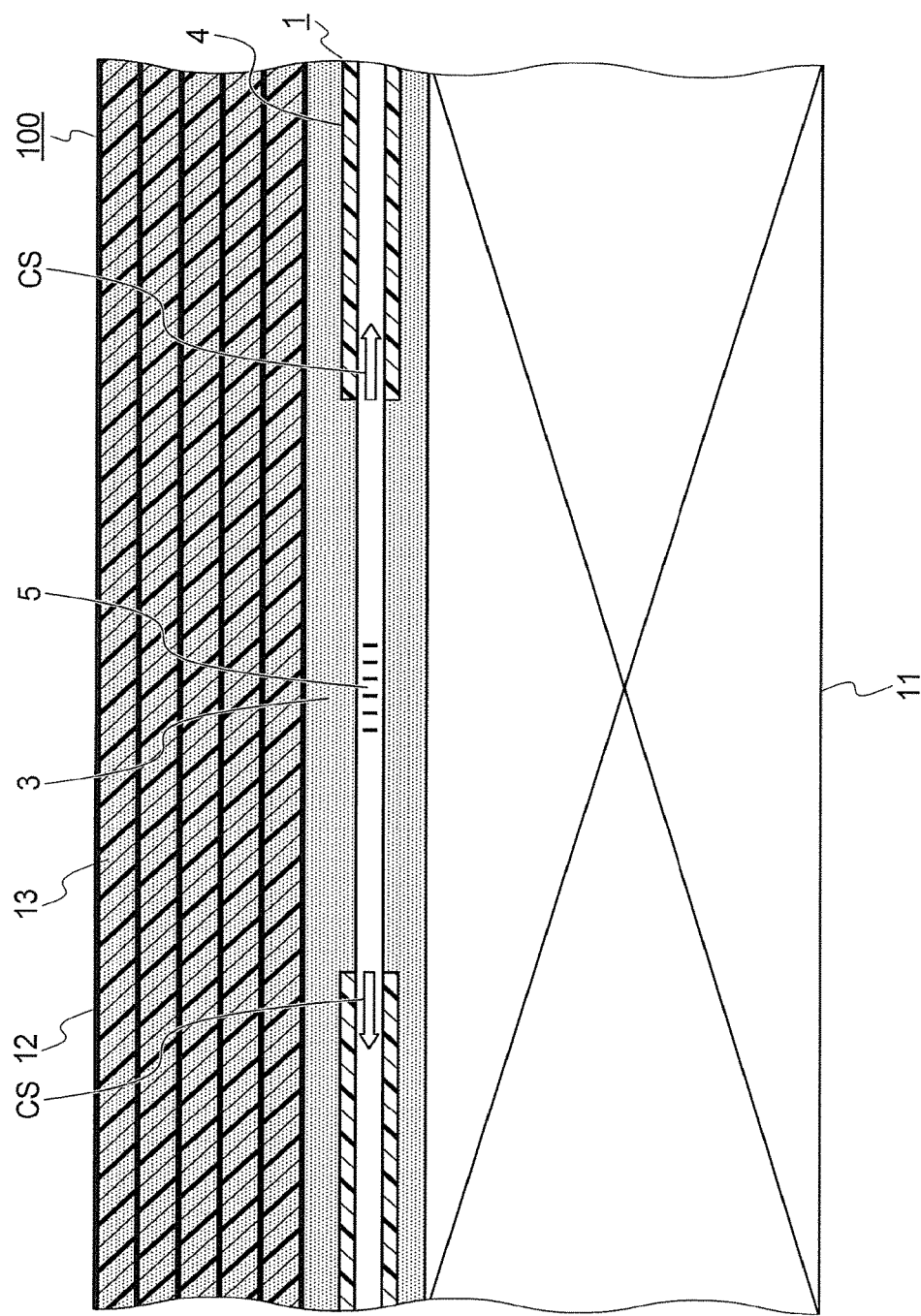

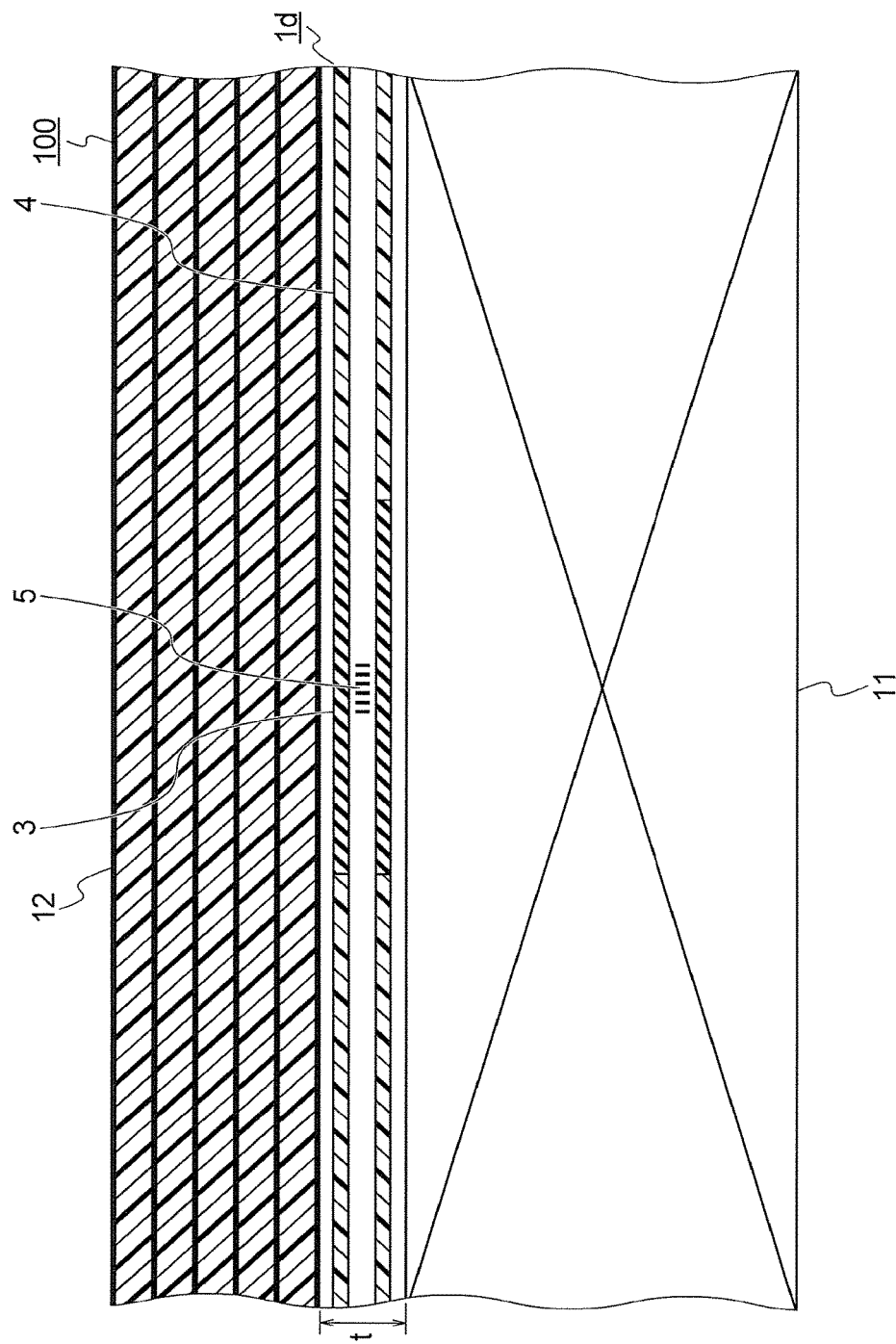

RESIN IMPREGNATION DETECTION DEVICE, COIL FOR ROTATING MACHINE, AND METHOD FOR IMPREGNATING AND MOLDING RESIN OF COIL FOR ROTATING MACHINE

TECHNICAL FIELD

The present invention relates to a resin impregnation detection device configured to detect impregnation with a liquid state resin in a narrow portion, a coil for a rotating machine, which includes the resin impregnation detection device, and a resin impregnation molding method for a coil for a rotating machine.

BACKGROUND ART

A coil to be used for a large power generator includes a coil conductor and coil insulation layers, which coat the coil conductor. The coil is manufactured by winding an insulation tape around the coil conductor, impregnating the insulation tape with an insulation resin of a low viscosity liquid state under a reduced pressure, and heating and curing the resin while press-molding the resin into a preset cross-sectional shape. When the large power generator coil is manufactured and a resin unimpregnated portion is generated in a resin impregnation process, insulation breakdown is concerned to occur from this unimpregnated portion.

It is required to sufficiently increase a time of the resin impregnation process to prevent the resin unimpregnated portion from being generated. However, when the time is increased more than necessary, productivity of coils is lowered. Therefore, the time is desired to be a minimum required time. A method for finishing the resin impregnation process within the sufficient and minimum required time includes two types of methods, namely, a method of predicting in advance a time required for resin filling, and a method of directly detecting resin filling.

According to the method of predicting a time required for resin filling, by performing precise numerical analysis and analyzing a resin impregnation flow, it is possible to predict a time at which the resin filling is finished. However, depending on a composition of the insulation tape and a condition during molding of an actual coil, a time at which the resin impregnation process is finished varies. Depending on the degree of variation, a time longer than the time predicted by the analysis may be required. When a difference between resin impregnation process finish times predicted by analysis and taken by actual molding is taken into account and a certain extended time is added to a predicted time of an analysis result, it is possible to prevent the resin unimpregnated portion from being generated by a variation in the resin impregnation process finish time. However, the extended time lowers productivity. It is conceivable that a suitable method for finishing the resin impregnation process within a minimum required time while preventing the resin unimpregnated portion from being generated by the variation is the method of directly detecting resin filling.

Conceivable means for detecting an arrival of a liquid to a specific position is firstly a method of visually observing the liquid. Impregnation with a resin takes place from an outer side to an inner side of a coil. Therefore, an innermost layer of an insulation layer is lastly filled with the resin. However, it is difficult to visually observe from the outside that the innermost layer is filled with the resin. Therefore, it is required to use a device capable of detecting resin impregnation to directly detect the resin filling.

Characteristics required for the resin impregnation detection device are the capability of accurately detecting resin impregnation, and a small size that allows the resin impregnation detection device to be installed in a narrow portion. The insulation layer before the resin impregnation is in a state in which an insulation tape is wound around a coil conductor, and the innermost layer is an extremely small region in which the coil conductor and the insulation tape are substantially in contact with each other. The resin impregnation detection device is required to be small to allow the resin impregnation detection device to be installed in the extremely small region between layers of the insulation tape and between the coil conductor and the insulation tape.

As a small detection device, there is given an optical fiber. The optical fiber includes a core at a center portion, and a clad, which covers the core. The optical fiber traps light in the core and propagates the light by reflecting the light on an interface between the core and the clad. The optical fiber has a thin outer diameter of approximately several hundreds of micrometers, and can be inserted even in a narrow portion between the coil conductor and the insulation tape.

Such a resin impregnation detection device including an optical fiber is, for example, a resin impregnation detection device including: an optical fiber; a coating resin layer, which coats the optical fiber; and a linear elastic body, which is disposed in parallel to the optical fiber under a state in which a tension is applied to an interior of the coating resin layer or an outer side of the coating resin layer (see, for example, Patent Literature 1). The coating resin layer is formed of a resin whose strength is to be lowered by contact with an impregnated resin being a detection target liquid. When the strength of the coating resin layer is lowered by the contact with the impregnated resin, the tension of the linear elastic body bends the optical fiber. When the optical fiber is bent, light leaks from the bent portion to an outside of the core, and optical loss occurs. Consequently, through measurement of this optical loss, it is possible to detect the resin impregnation.

CITATION LIST

Patent Literature

[PTL 1] JP 11-94688 A

SUMMARY OF INVENTION

Technical Problem

However, the related art has the following problem.

According to the related art described in Patent Literature 1, as described above, the linear elastic body is buried under a state in which the tension is applied to the coating resin layer around the optical fiber. Contact of the impregnated resin with the coating resin layer lowers the strength of the coating resin layer, and the tension of the linear elastic body bends the optical fiber. Then, resin impregnation is detected based on optical loss at the bent portion.

In the related art, the linear elastic body is buried in a sensor, and thus the diameter of a portion of the sensor is thicker than that of a portion of the optical fiber other than the sensor. There is a problem in that, even in a case where the diameter of the optical fiber is thin, when the sensor makes the diameter thick, it is difficult to insert the optical fiber in a narrow portion. Moreover, there is another problem in that there is a metal foreign material, which is the linear elastic body, in the sensor, and the linear elastic body remains in a product even after resin impregnation.

The present invention has been made to solve the above-mentioned problem, and provides a resin impregnation detection device, which can be inserted in a narrow portion, is capable of detecting impregnation with a liquid resin, and does not leave metal foreign materials other than an optical fiber in a product even after the resin impregnation. Moreover, the present invention provides a coil for a rotating machine, which includes the resin impregnation detection device having the above-mentioned features, and a resin impregnation molding method for a coil for a rotating machine.

Solution to Problem

According to one embodiment of the present invention, there is provided, for example, a resin impregnation detection device including: an optical fiber including at least one FBG sensor; and a coating resin, which is coated by applying a compressive strain to the FBG sensor when being cured, wherein the coating resin includes a resin to be softened by contact with a detection target resin, and wherein the resin impregnation detection device is configured to detect impregnation with the resin by the FBG sensor, which is configured to detect, when the compressive strain applied to the FBG sensor is released during the softening, a change in a Bragg wavelength caused by the release of the compressive strain.

Advantageous Effects of Invention

According to the present invention, by applying to the FBG sensor in advance a compressive strain caused by cure shrinkage of the coating resin or heat shrinkage thereof from a curing temperature to a normal temperature, when the coating resin is softened by contact with the impregnated resin, the compressive strain is released. It is possible to provide the resin impregnation detection device capable of detecting resin impregnation by detecting a strain difference in this case. The resin impregnation detection device includes only the optical fiber and the coating resin layer, and does not include foreign materials. Consequently, the resin impregnation detection device is only required to have the minimum required thickness of the coating resin layer, can be easily inserted in a narrow portion, and does not leave foreign materials other than the optical fiber.

BRIEF DESCRIPTION OF DRAWINGS

FIG. 9A and FIG. 9B are each a schematic view for illustrating a process during which the coating resin around the FBG sensor shrinks in the first embodiment of the present invention.

FIG. 10 is a schematic view for illustrating a state in which the resin impregnation detection device is disposed between a coil conductor and an insulation tape in a coil for a rotating machine according to the first embodiment of the present invention.

FIG. 11 is a schematic view for illustrating a state in which a portion around the FBG sensor of the resin impregnation detection device is filled with an impregnated resin in the coil for a rotating machine according to the first embodiment of the present invention.

FIG. 20 is a schematic view for illustrating a state in which a resin impregnation detection device is disposed between the coil conductor and the insulation tape in the coil for a rotating machine according to the fifth embodiment of the present invention.

DESCRIPTION OF EMBODIMENTS

Now, a resin impregnation detection device, a coil for a rotating machine, and a resin impregnation molding method for a coil for a rotating machine according to each of the embodiments of the present invention are described with reference to drawings. The same or corresponding portions are denoted by the same reference symbols in each of the embodiments, and overlapping description thereof is omitted.

First Embodiment

Figure 1:
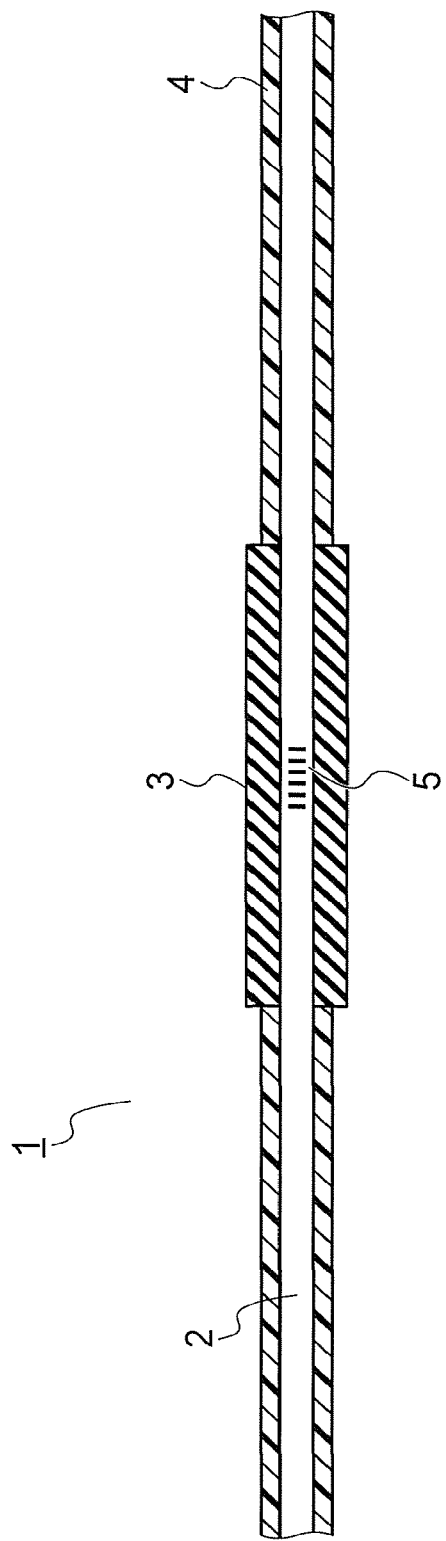
FIG. 1 is a schematic view for illustrating a resin impregnation detection device according to a first embodiment of the present invention.

FIG. 1 is a schematic view for illustrating a resin impregnation detection device according to a first embodiment of the present invention. As illustrated in FIG. 1, a resin impregnation detection device 1 includes an optical fiber 2, a coating resin 3, a protection coating 4, and an FBG sensor 5. Around the FBG sensor 5, the protection coating 4 is removed, and the optical fiber 2 is coated with the coating resin 3. The FBG sensor 5 includes a fiber Bragg grating formed in the optical fiber 2.

The coating resin 3 is a resin to be softened by a solvent. When the resin impregnation detection device 1 is applied to detection of resin impregnation in a coil of a power generator or the like, a narrow insulation tape is required to be impregnated with a detection target resin. Therefore, the resin includes the solvent as a reactive diluent to achieve low viscosity. Examples of such a resin include a styrene resin and an acrylic resin. The coating resin 3 is one of those resins that are softened by contact with a solvent. Examples of the coating resin 3 include an acrylic resin, a vinyl chloride resin, a polystyrene resin, and a polyvinyl alcohol resin. The coating resin 3 is only required to be a resin to be softened by contact with a solvent, and a resin type is not particularly limited. An appropriate resin is selected in accordance with the detection target resin, more specifically, a type of a solvent of the resin.

Next, a method of detecting resin impregnation by the resin impregnation detection device according to the first embodiment is described with reference to FIG. 2 to FIG. 5.

Figure 2:
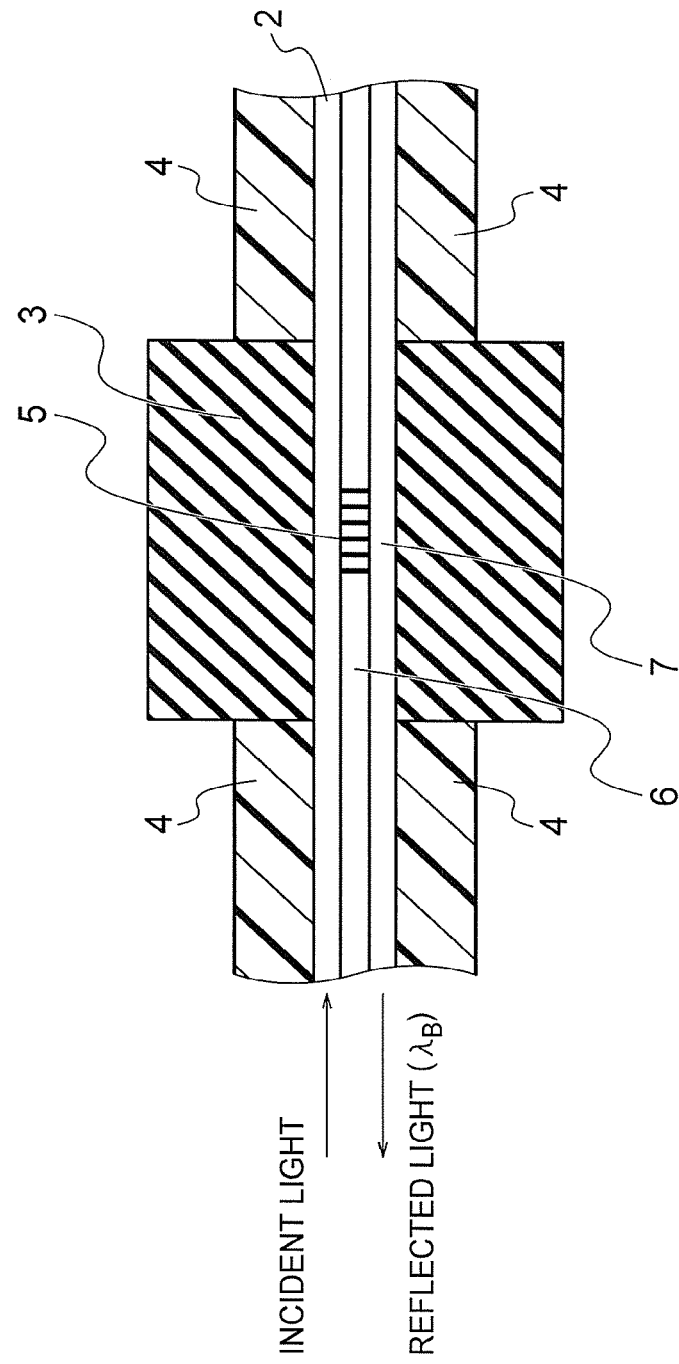
FIG. 2 is an enlarged view for illustrating a vicinity of an FBG sensor of an optical fiber of the resin impregnation detection device according to the first embodiment of the present invention.

FIG. 2 is an enlarged view for illustrating a vicinity of the FBG sensor 5 of the optical fiber 2.

Figure 3:
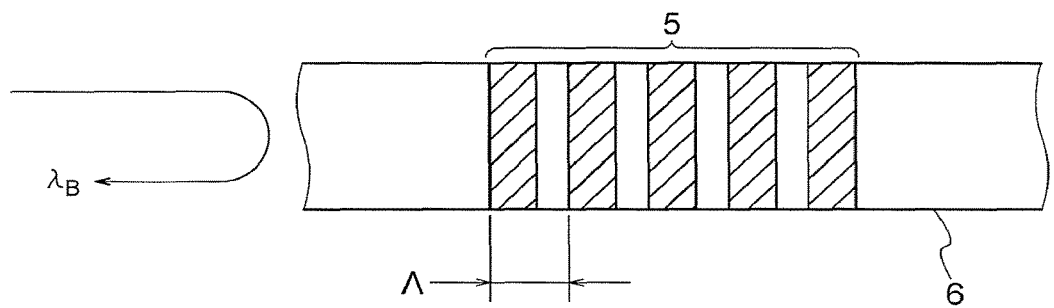
FIG. 3 is a schematic view for illustrating the structure of the FBG sensor of the resin impregnation detection device according to the first embodiment of the present invention.

FIG. 3 is a schematic view for illustrating the structure of the FBG sensor 5.

Figure 4:
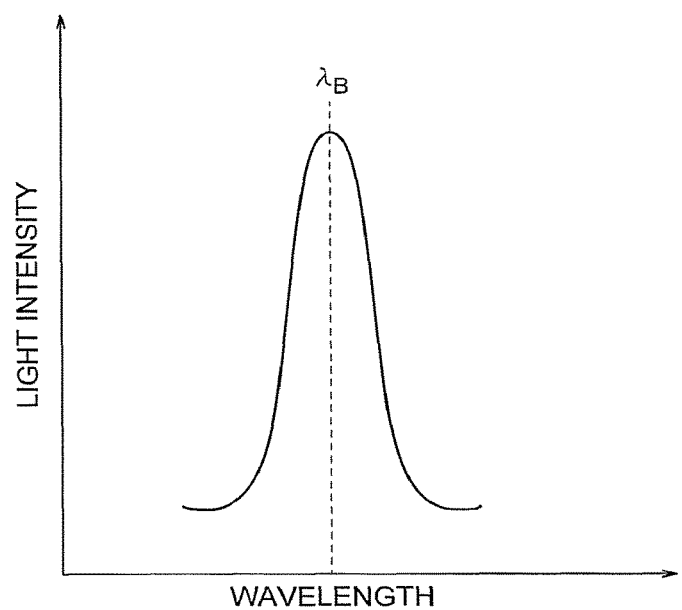
FIG. 4 is a graph for showing reflection spectrum characteristics of the FBG sensor of the resin impregnation detection device according to the first embodiment of the present invention.

FIG. 4 is a graph for showing reflection spectrum characteristics of the FBG sensor 5.

Figure 5:
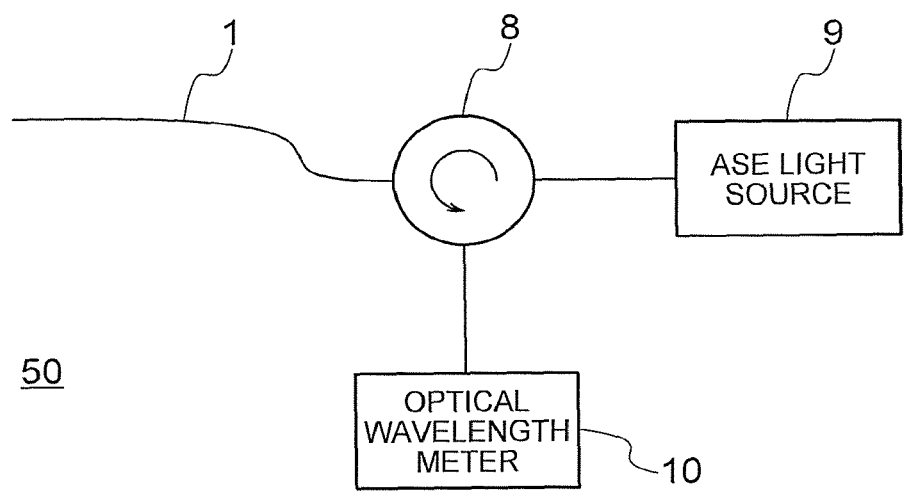
FIG. 5 is a configuration diagram for illustrating a strain detecting system, which uses the resin impregnation detection device according to the first embodiment of the present invention.

FIG. 5 is a configuration diagram for illustrating a strain detecting system 50, which uses the resin impregnation detection device 1.

The optical fiber 2 illustrated in FIG. 2 includes a core 6, a clad 7, which covers an outer surface of the core 6, and the protection coating 4, which covers an outer surface of the clad 7. In the vicinity of the FBG sensor 5, the protection coating 4 is removed, and the clad 7 is exposed.

For example, regarding the sizes, the diameter of the core 6 is approximately 10 μm, the diameter of the clad 7 is approximately 125 μm, and the entire diameter of the optical fiber 2 including the core 6, the clad 7, and the protection coating 4 is approximately 250 μm. The FBG sensor 5 is formed over a range of approximately 5 mm in the core 6 along an axial direction of the optical fiber 2.

As illustrated in FIG. 3, the FBG sensor 5 has a cyclic structure of an effective refractive index formed in the core 6, and has a feature that steep reflection spectrum characteristics shown in FIG. 4 can be obtained. In the FBG sensor 5 illustrated in FIG. 3, the effective refractive index of the core 6 changes at a cycle length $\Lambda$.

A relationship among a Bragg wavelength $\lambda_B$, which is a center wavelength of the reflection spectrum in FIG. 4, a grating cycle $\Lambda$, which indicates an interval of a diffraction grating illustrated in FIG. 3, and an effective refractive index n of the diffraction grating is expressed by Expression (1).

$$\lambda_B = 2n\Lambda \quad (1)$$

The effective refractive index n depends on temperature, and the cycle $\Lambda$ depends on temperature and strain. Consequently, when the strain occurs in the FBG sensor 5, the Bragg wavelength $\lambda_B$ changes based on Expression (1), and hence it is possible to detect the strain.

The strain detecting system 50 illustrated in FIG. 5 includes the resin impregnation detection device 1, an optical circulator 8, an ASE light source 9, and an optical wavelength meter 10.

When the strain is to be detected, the optical circulator 8, which is configured to convert an optical path, is connected to a base end of the resin impregnation detection device 1. The optical circulator 8 is connected to the amplified spontaneous emission (ASE) light source 9, which is a broadband light source, and the optical wavelength meter 10, which is a wavelength measurement device. This system can measure the Bragg wavelength $\lambda_B$, and can detect the strain based on the change in the Bragg wavelength $\lambda_B$. When the strain is applied in advance to the FBG sensor 5 and this strain is released during resin impregnation, the strain detecting system illustrated in FIG. 5 detects a strain change caused by the release of the strain, and thus it is possible to detect the resin impregnation.

Next, a method of manufacturing the resin impregnation detection device 1 according to the first embodiment is described with reference to FIG. 6 to FIGS. 9A and 9B.

Figure 6:
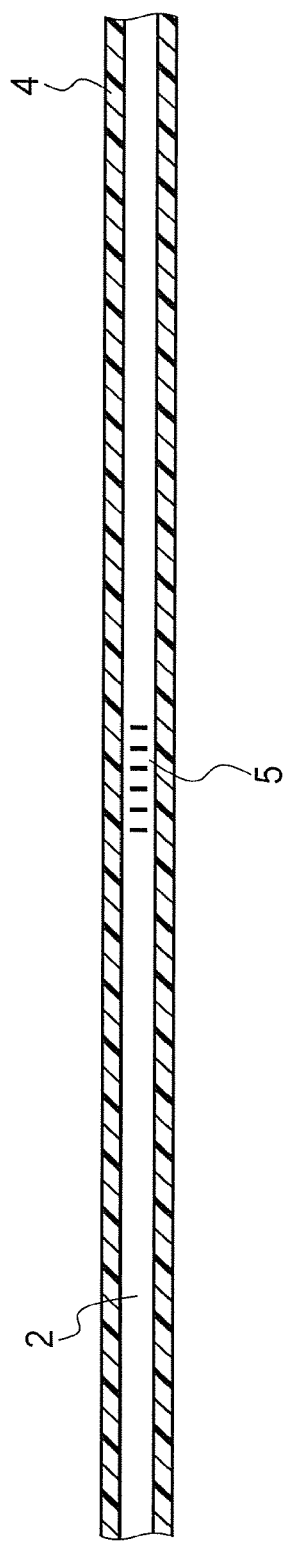
FIG. 6 is a schematic view for illustrating an optical fiber in the first embodiment of the present invention.

FIG. 6 is a schematic view for illustrating the optical fiber 2.

Figure 7:
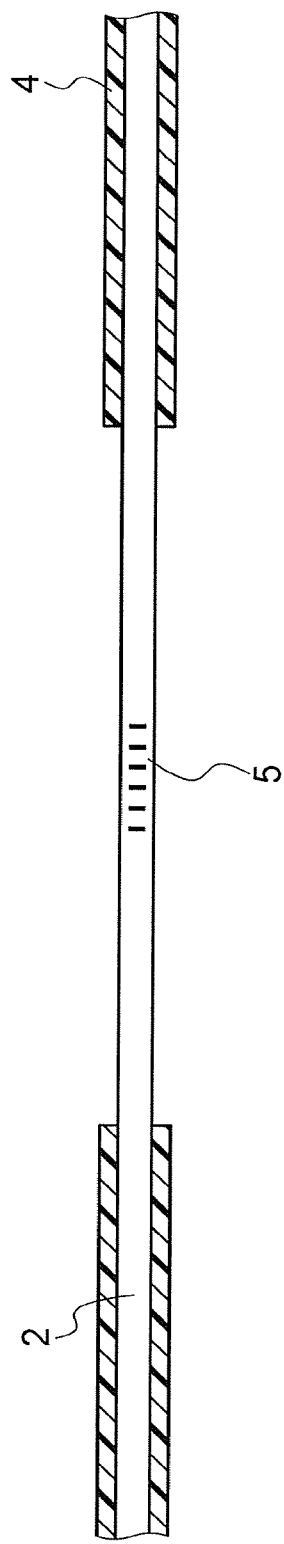
FIG. 7 is a schematic view for illustrating a state in which a protection coating around the FBG sensor is removed in the first embodiment of the present invention.

FIG. 7 is a schematic view for illustrating a state in which the protection coating 4 around the FBG sensor 5 is removed.

Figure 8:
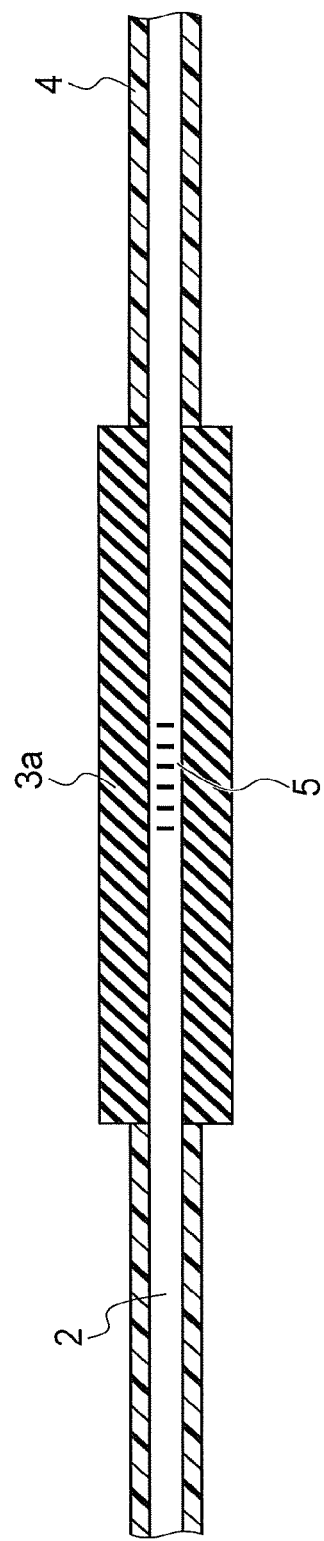
FIG. 8 is a schematic view for illustrating a state in which an uncured coating resin is applied around the FBG sensor in the first embodiment of the present invention.

FIG. 8 is a schematic view for illustrating a state in which an uncured coating resin 3a is applied around the FBG sensor 5.

FIGS. 9A and 9B are each a schematic view for illustrating a process during which the uncured coating resin 3a around the FBG sensor 5 shrinks.

As illustrated in FIG. 6, the optical fiber 2 includes the FBG sensor 5 inside, and the protection coating 4 coats around the optical fiber 2. The protection coating 4 coats around the FBG sensor 5 before the protection coating 4 is removed. In this state, the strain change cannot be detected. Therefore, it is required to remove the protection coating 4 around the FBG sensor 5 as illustrated in FIG. 7 to expose the FBG sensor 5.

After the FBG sensor 5 is exposed, the uncured coating resin 3a is applied around the FBG sensor 5 as illustrated in FIG. 8. The uncured coating resin 3a is adhered to a surface of the optical fiber 2 during a curing process, and, at the same time, shrinks from an uncured state by way of cure shrinkage. Moreover, when the uncured coating resin 3a is a heat curing resin, the coating resin thermally shrinks while the temperature lowers from a curing temperature to a normal temperature. When the temperature of the coating resin 3a at the curing temperature illustrated in FIG. 9A lowers to the normal temperature, the coating resin 3a shrinks as illustrated in FIG. 9B. Accordingly, the FBG sensor 5 also shrinks, and a compressive strain remains in the FBG sensor 5 as indicated by an arrow CS. Through the above-mentioned process, the resin impregnation detection device 1 is manufactured.

A magnitude of the remaining compressive strain is determined based on a cure shrinkage ratio or a linear expansion coefficient of the coating resin 3, and, in addition, an elastic modulus. The large magnitude of the remaining strain is preferred in order to precisely detect the strain change. As a type of the coating resin 3, a resin having a high cure shrinkage ratio or a linear expansion coefficient, and, in addition, a high elastic modulus is more suitable.

Next, a resin impregnation detecting method to be performed by the resin impregnation detection device 1 is described with reference to FIG. 10 and FIG. 11.

FIG. 10 is a schematic view for illustrating a state in which the resin impregnation detection device 1 is disposed between a coil conductor 11 and an insulation tape 12.

FIG. 11 is a schematic view for illustrating a state in which a portion around the FBG sensor 5 of the resin impregnation detection device 1 is filled with an impregnated resin 13.

In a state before the resin impregnation process, in a coil 100 for a rotating machine, for example, a power generator, a plurality of layers of the insulation tape 12 are wound around the coil conductor 11 to form coil insulation layers. As illustrated in FIG. 10, the resin impregnation detection device 1 is disposed between the coil conductor 11 and the insulation tape 12 of the coil 100 for a rotating machine. The insulation tape 12 is impregnated with the impregnated resin 13 from an outside to an inner side as seen from the coil conductor 11, that is, from the top to the bottom in FIG. 10. Therefore, the resin impregnation detection device 1 is disposed in a layer on an inner layer side of the insulation tape 12, and is more preferred to be disposed in an innermost layer of the insulation tape 12. Consequently, when the resin impregnation detection device 1 is disposed in the innermost layer, it is possible to detect that the innermost layer of the insulation tape 12 is filled with the impregnated resin 13.

When the innermost layer is filled with the impregnated resin 13, the coating resin 3 of the resin impregnation detection device 1 is softened by contact with the solvent contained in the impregnated resin 13. The compressive strain remains on the FBG sensor 5 of the resin impregnation detection device 1 as described above. Consequently, when the coating resin 3 is softened, the compressive strain is released as indicated by the arrow CS in FIG. 11. When the strain detecting system 50 illustrated in FIG. 5 detects the change in the strain at this time, the strain detecting system 50 can detect resin impregnation.

A coil provided with the resin impregnation detection device 1 between the coil conductor 11 and the insulation tape 12 is heated and subjected to press molding after the resin impregnation. Both the impregnated resin 13 and the coating resin 3 are integrally formed into an insulation layer. Consequently, coil characteristics are not influenced.

The resin impregnation detection device employing this configuration can be inserted in a narrow portion, is capable of detecting impregnation with a liquid resin, and does not leave metal foreign materials other than the optical fiber in a product even after the resin impregnation.

Second Embodiment

A resin impregnation detection device according to a second embodiment of the present invention differs from the resin impregnation detection device according to the first embodiment in an application range of the coating resin 3. The resin impregnation detection device according to the second embodiment has the same configuration as that of the first embodiment other than the application range of the coating resin 3.

A method of manufacturing a resin impregnation detection device 1 according to the second embodiment is described with reference to FIG. 12 and FIGS. 13A and 13B.

Figure 12:
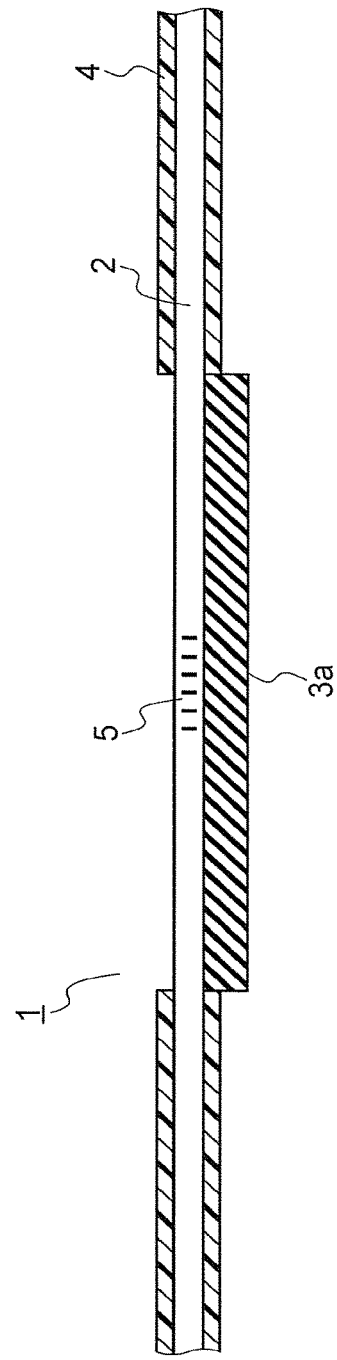
FIG. 12 is a schematic view for illustrating a state in which an uncured coating resin is applied only to a half surface of the FBG sensor in a circumferential direction thereof around the FBG sensor in a second embodiment of the present invention.

FIG. 12 is a schematic view for illustrating a state in which the uncured coating resin 3*a* is applied only to a half surface of the FBG sensor 5 in a circumferential direction thereof around the FBG sensor 5.

Figure 13A:
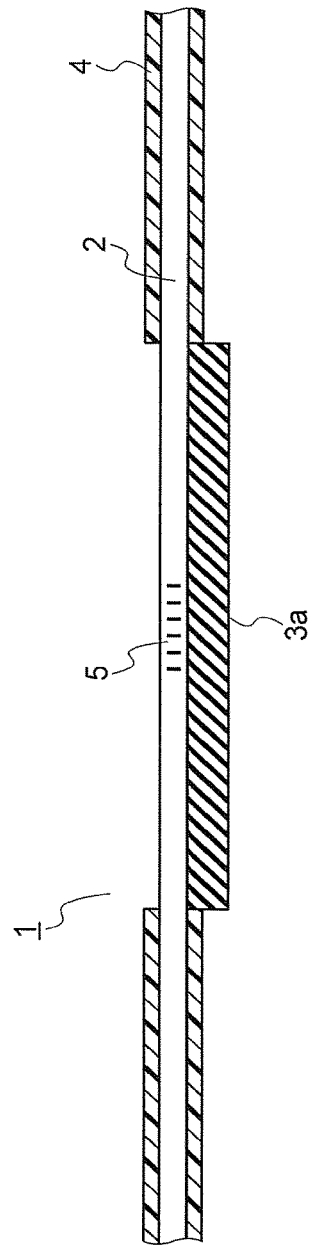
FIG. 13A and FIG. 13B are each a schematic view for illustrating a process during which the uncured coating resin around the FBG sensor in the second embodiment of the present invention shrinks.
Figure 13B:
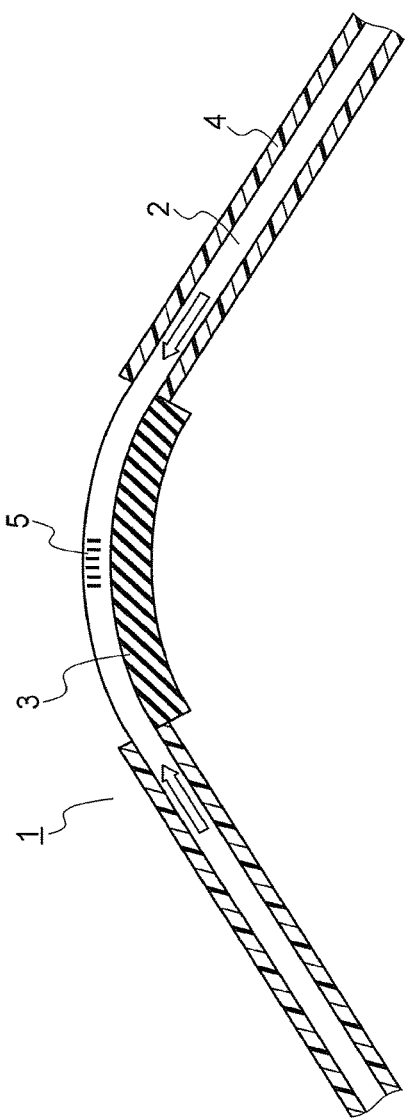

FIGS. 13A and 13B are each a schematic view for illustrating a process during which the uncured coating resin 3*a* around the FBG sensor 5 shrinks.

When the uncured coating resin 3*a* is applied only to the half surface of the FBG sensor 5 in the circumferential direction around the FBG sensor 5 as illustrated in FIG. 12, the optical fiber 2 bends as illustrated in FIGS. 13A and 13B from a straight state illustrated in FIG. 13A toward a side applied with the uncured coating resin 3*a* as illustrated in FIG. 13B. This bend leaves a compressive strain on the FBG sensor 5.

The optical fiber 2 has a high elastic modulus, and depending on the type of the coating resin 3, it is difficult to apply a sufficient compressive strain to the FBG sensor 5 by cure shrinkage. In such a case, by causing the optical fiber 2 to bend by the above-mentioned method, it is possible to apply the compressive strain to the FBG sensor 5.

Similarly to the first embodiment, the resin impregnation detection device employing this configuration can be inserted in a narrow portion, is capable of detecting impregnation with a liquid resin, and does not leave foreign materials other than the optical fiber in a product even after the resin impregnation.

Third Embodiment

A resin impregnation detection device according to a third embodiment of the present invention differs from the resin impregnation detection device according to the first embodiment in positions and the number of resin impregnation detection devices to be disposed. The resin impregnation detection device according to the third embodiment has the same configuration as that of the first embodiment other than the positions and the number of the resin impregnation detection device to be disposed.

A resin impregnation detecting method for the resin impregnation detection device according to the third embodiment is described with reference to FIG. 14 and FIG. 15.

Figure 14:
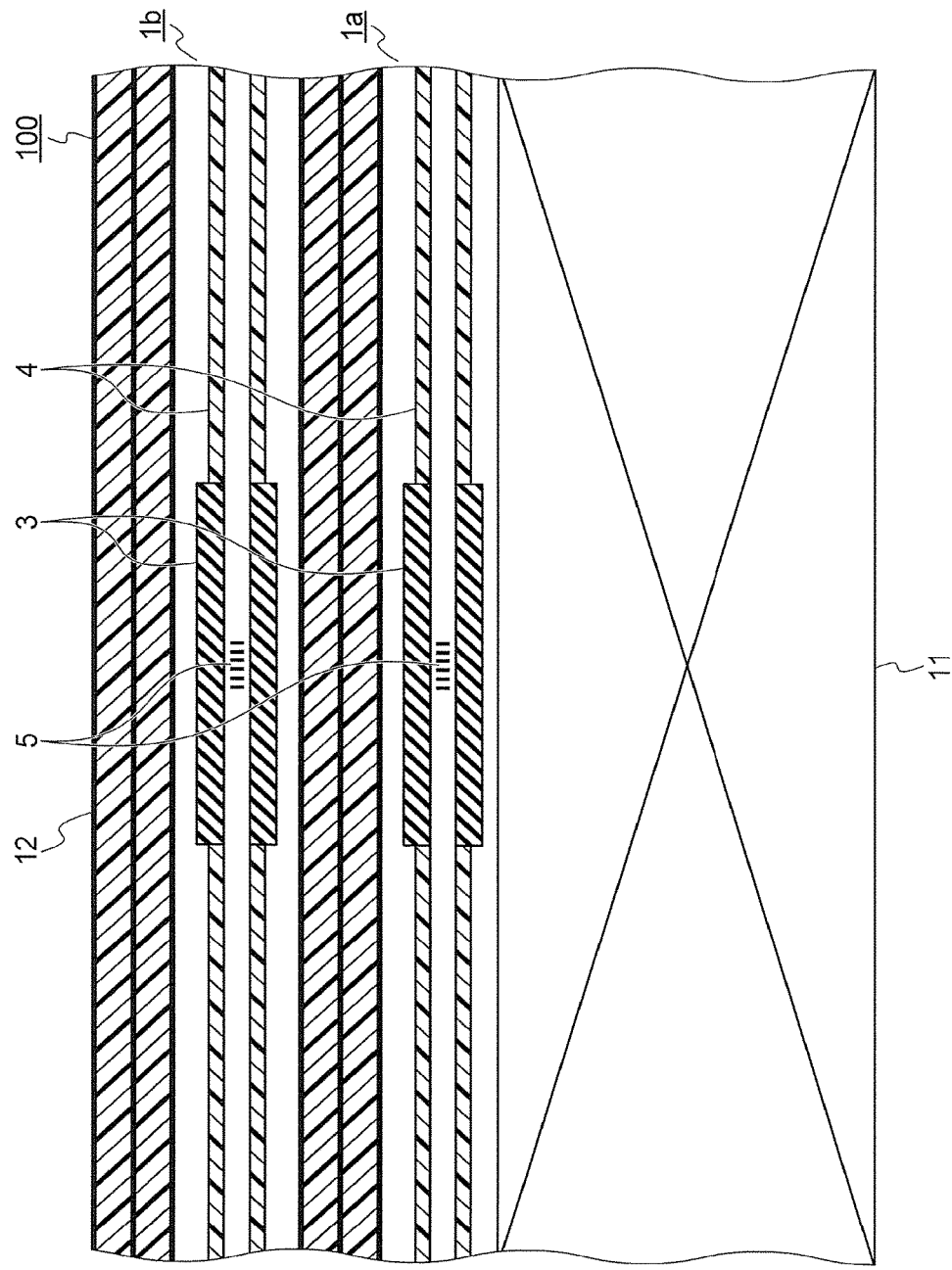
FIG. 14 is a schematic view for illustrating a state in which the resin impregnation detection devices are disposed between the coil conductor and the insulation tape, and between layers of the insulation tape in the coil for a rotating machine according to a third embodiment of the present invention, respectively.

FIG. 14 is a schematic view for illustrating a state in which resin impregnation detection devices 1*a* and 1*b* are disposed between the coil conductor 11 and the insulation tape 12 and between the layers of the insulation tape 12, respectively.

Figure 15:
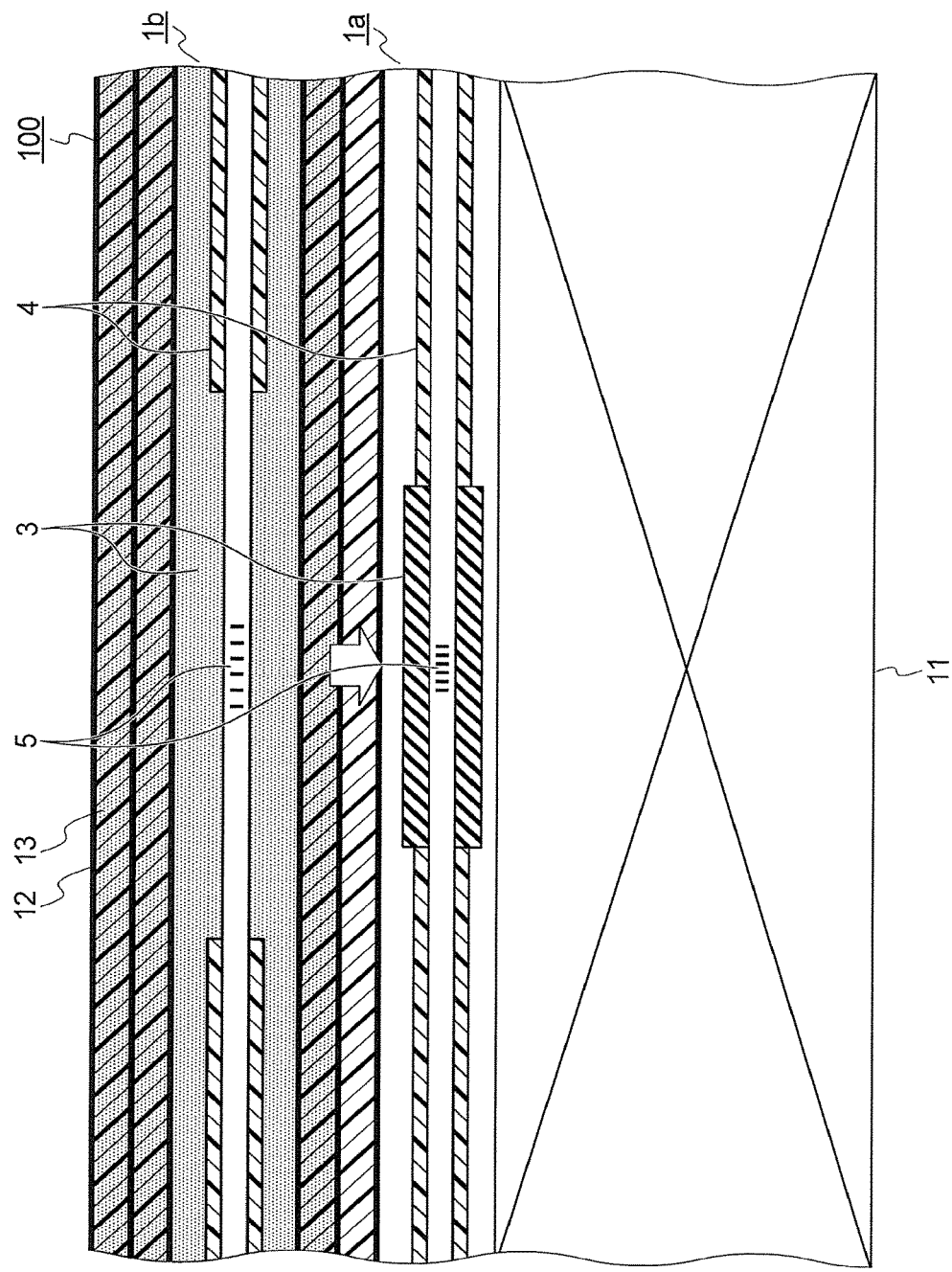
FIG. 15 is a schematic view for illustrating a state in which portions around the FBG sensor of the resin impregnation detection device disposed between the layers of the insulation tape are filled with an impregnated resin in the coil for a rotating machine according to the third embodiment of the present invention.

FIG. 15 is a schematic view for illustrating a state in which portions around the FBG sensor 5 of the resin impregnation detection device 1*b* disposed between the layers of the insulation tape 12 are filled with an impregnated resin.

As illustrated in FIG. 14, the resin impregnation detection device may be disposed not only between the coil conductor 11 and the insulation tape 12 as represented by the resin impregnation detection device 1*a*, but also between the layers of the insulation tape 12 as represented by the resin impregnation detection device 1*b*. Impregnation with the impregnated resin 13 takes place from an outer side to an inner side, and hence, when the resin impregnation detection device 1*b* is also disposed between the layers of the insulation tape 12, the resin impregnation detection device 1*b* disposed between the layers of the insulation tape 12 as illustrated in FIG. 15 detects resin impregnation earlier than the resin impregnation detection device 1a disposed between the coil conductor 11 and the insulation tape 12. Consequently, it is possible to monitor in detail a resin impregnation situation between the layers of the insulation tape 12, which is difficult to observe, to thereby improve an impregnation process and resin impregnation analysis precision.

When, for example, the coil 100 for a rotating machine is to be formed with use of the resin impregnation detection device 1 in the resin impregnation forming method for a coil for a rotating machine according to the present invention, as illustrated in FIG. 14, the resin impregnation detection device 1 is disposed at, for example, at least one of a portion between the coil conductor 11 and the insulation tape 12, which forms coil insulation layers on the outer side of the coil conductor 11, and a portion between the layers of the insulation tape 12, and the insulation tape (12) is wound around the resin impregnation detection device 1.

Next, as illustrated in FIG. 15, the coil 100 for a rotating machine is impregnated with the impregnated resin 13 from the outer side thereof. Until all disposed resin impregnation detection devices 1 detect resin impregnation with the impregnated resin 13, the resin impregnation is continued.

Similarly to the first embodiment, the resin impregnation detection device employing this configuration can be inserted in a narrow portion, is capable of detecting impregnation with a liquid resin, and does not leave metal foreign materials other than the optical fiber in a product even after the resin impregnation.

Fourth Embodiment

A resin impregnation detection device according to a fourth embodiment of the present invention differs from the resin impregnation detection device according to the first embodiment in the number of FBG sensors included in the resin impregnation detection device, and includes a plurality of FBG sensors. The resin impregnation detection device according to the fourth embodiment has the same configuration as that of the first embodiment other than the number of FBG sensors.

The resin impregnation detection device according to the fourth embodiment is described with reference to FIG. 16 to FIG. 18.

Figure 16:
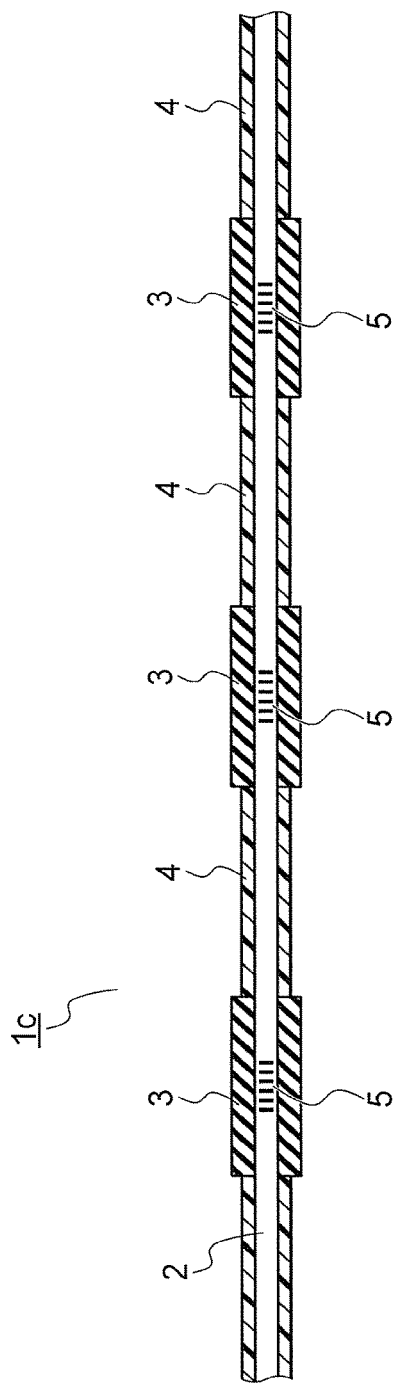
FIG. 16 is a schematic view for illustrating a resin impregnation detection device including a plurality of FBG sensors according to a fourth embodiment of the present invention.

FIG. 16 is a schematic view for illustrating a resin impregnation detection device 1c including a plurality of FBG sensors.

Figure 17:
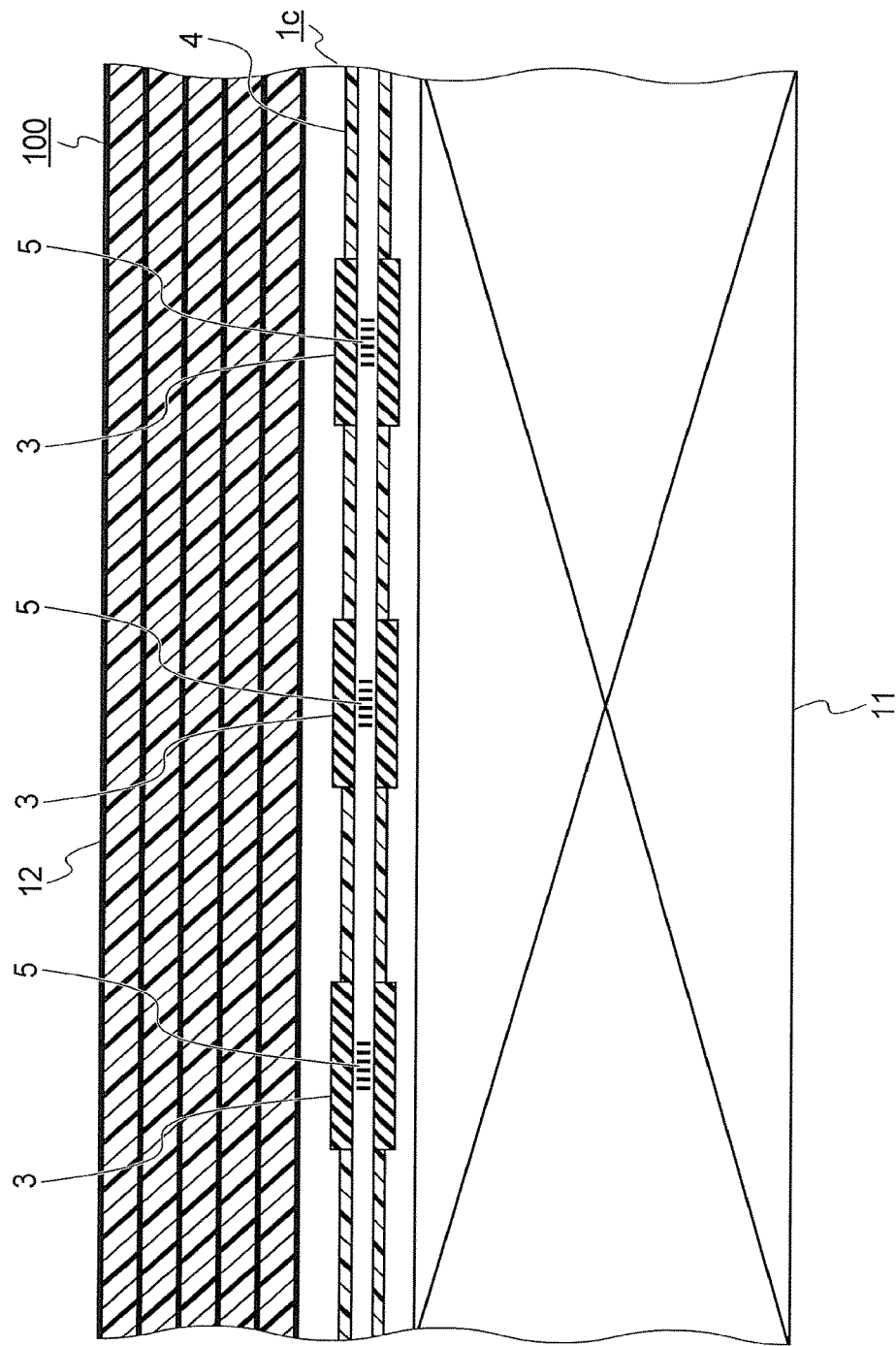
FIG. 17 is a schematic view for illustrating a state in which the resin impregnation detection device including the plurality of FBG sensors is disposed between the coil conductor and the insulation tape in the coil for a rotating machine according to the fourth embodiment of the present invention.

FIG. 17 is a schematic view for illustrating a state in which the resin impregnation detection device 1c including the plurality of FBG sensors is disposed between the coil conductor 11 and the insulation tape 12.

Figure 18:
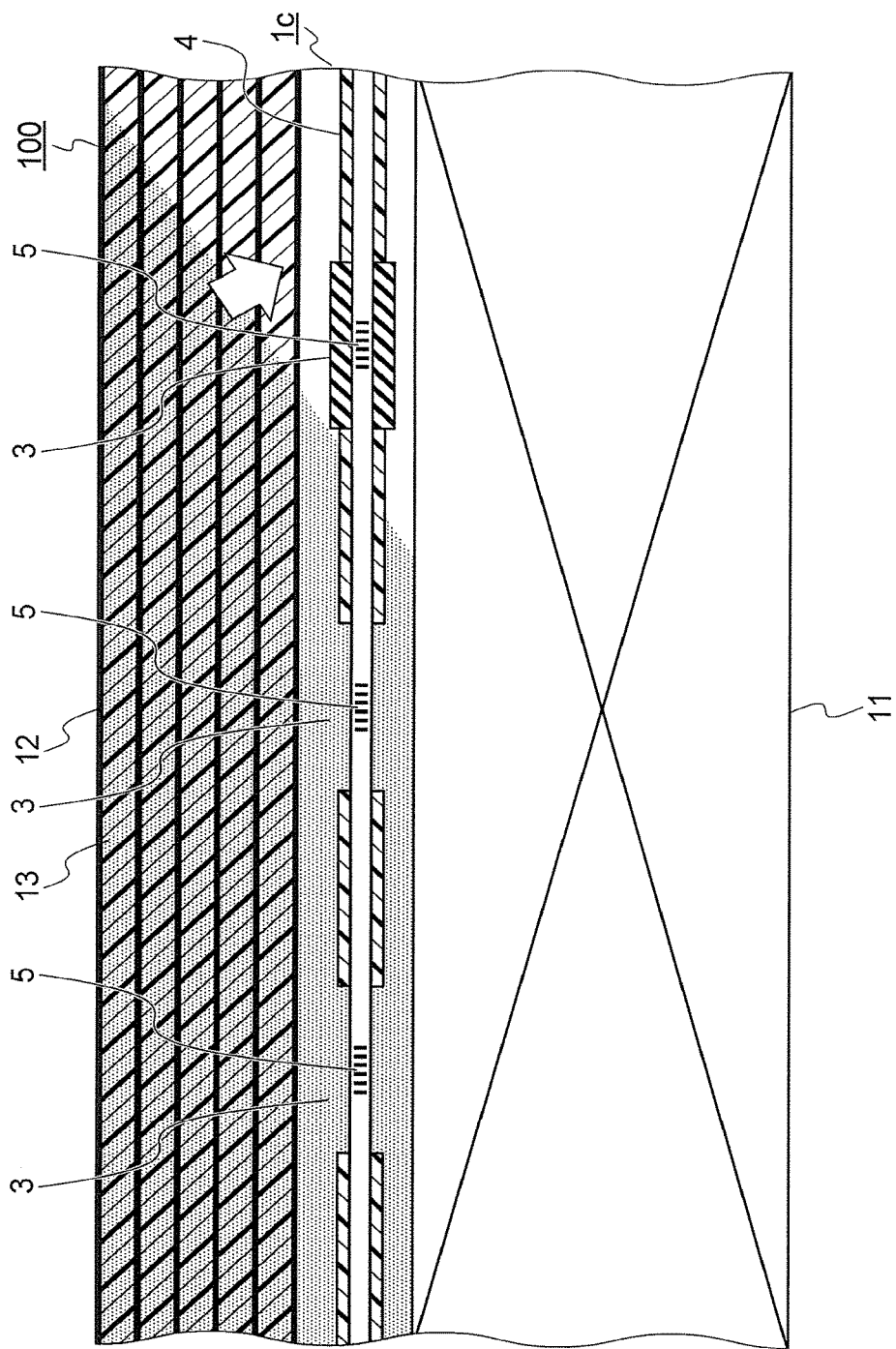
FIG. 18 is a schematic view for illustrating a state in which portions around part of the FBG sensors of the resin impregnation detection device including the plurality of FBG sensors are filled with the impregnated resin in the coil for a rotating machine according to the fourth embodiment of the present invention.

FIG. 18 is a schematic view for illustrating a state in which portions around part of the FBG sensors of the resin impregnation detection device 1c including the plurality of FBG sensors are filled with the impregnated resin 13.

As illustrated in FIG. 16, the resin impregnation detection device 1c may include a plurality of FBG sensors 5a to 5c. In the fourth embodiment, an example in which three FBG sensors are provided is illustrated. However, the number of FBG sensors is not limited thereto. In the resin impregnation detection device 1, through connection of the three FBG sensors 5a to 5c having different Bragg wavelengths $\lambda_B$, which are center wavelengths of reflection spectra, to each other in series by the optical fiber 2, multipoint FBG sensors can be implemented. When the FBG sensors are formed by providing the above-mentioned coating resin 3 to each of the multipoint FBG sensors 5a to 5c, the one resin impregnation detection device 1c can monitor resin impregnation situations at a plurality of portions.

In the resin impregnation process for a coil 100 for a rotating machine, impregnation with the impregnated resin 13 takes place from an outer side to an inner side, and, at the same time, the impregnated resin 13 moves from a coil end to a center, that is, in a horizontal direction from left to right in FIG. 18, for example. As illustrated in FIG. 17, when the resin impregnation detection device 1c including the plurality of FBG sensors 5a to 5c is deposited between the coil conductor 11 and the insulation tape 12 of the coil 100 for a rotating machine, it is possible to monitor the resin impregnation situation in an axial direction of the coil conductor 11, which is the horizontal direction in FIG. 17. When portions around part of the FBG sensors 5a and 5b illustrated in FIG. 18 are filled with the impregnated resin 13, it is possible to assume that a flow distal end of the impregnated resin 13 is positioned between the FBG sensor 5b, which has already detected resin impregnation, and the FBG sensor 5c, which has not yet detected the resin impregnation.

In resin impregnation molding, it is only required to be determined that resin impregnation is reliably completed, and it may not necessarily required to be determined immediately after impregnation that the resin impregnation is completed. Even in a case where, for example, a time taken for softening is approximately several minutes, when the time required for softening in each FBG sensor is the same or substantially the same, it is possible to monitor an impregnation situation based on a difference between the times.

Similarly to the first embodiment, the resin impregnation detection device employing this configuration can be inserted in a narrow portion, is capable of detecting impregnation with a liquid resin, and does not leave metal foreign materials other than the optical fiber in a product even after the resin impregnation.

Fifth Embodiment

A resin impregnation detection device according to a fifth embodiment of the present invention differs from the resin impregnation detection device according to the first embodiment in that the diameter of the coating resin of the resin impregnation detection device differs, and the diameter of the coating resin and the diameter of the protection coating are the same or substantially the same. The resin impregnation detection device according to the fifth embodiment has the same configuration as that of the first embodiment other than the diameter of the coating resin.

A resin impregnation detection device 1 according to the fifth embodiment is described with reference to FIG. 19 and FIG. 20.

Figure 19:
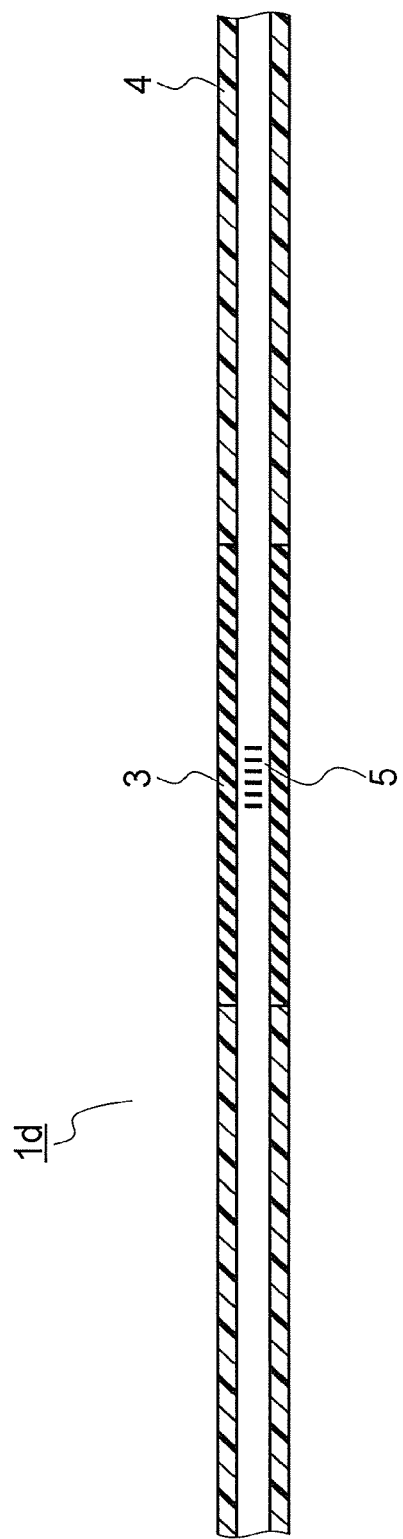
FIG. 19 is a schematic view for illustrating a resin impregnation detection device according to a fifth embodiment of the present invention.

FIG. 19 is a schematic view for illustrating a resin impregnation detection device 1d.

FIG. 20 is a schematic view for illustrating a state in which the resin impregnation detection device 1d is disposed between the coil conductor 11 and the insulation tape 12 of the coil 100 for a rotating machine.

Whether or not the resin impregnation detection device 1d can be inserted in a narrow portion is determined based on the diameter of the coating resin 3 and the diameter of the protection coating 4. From the viewpoint of applying a remaining strain to the FBG sensor 5, the diameter of the coating resin 3 is preferred to be large. However, when the diameter of the coating resin 3 is increased too much, the coating resin 3 may not be inserted to the narrow portion. The diameter of the protection coating 4 is determined at a point in time at which the optical fiber 2 has been purchased, and therefore is difficult to adjust by oneself. Consequently, when the diameter of the coating resin 3 is made to be the same or substantially the same as the diameter of the protection coating 4 as illustrated in FIG. 19, the resin impregnation detection device 1d can be inserted to any portion as long as the portion is a portion in which the optical fiber 2 can be inserted.

In a case where the resin impregnation detection device 1 according to the fifth embodiment is disposed between the coil conductor 11 and the insulation tape 12, when the diameter of the coating resin 3 is the same or substantially the same as the diameter of the protection coating 4, it is possible to minimize a gap t between the coil conductor 11 and the insulation tape 12 as illustrated in FIG. 20, to thereby minimize an influence on resin impregnation by the resin impregnation detection device 1d.

In each of the above-mentioned embodiments, the coating resin 3 is formed over the FBG sensor 5 and preset regions of the FBG sensor 5 on both sides in the axial direction of the optical fiber 2 to apply a great compressive strain to the FBG sensor 5. Those regions are defined as FBG sensor regions. The coating resin 3a shrinks when the temperature lowers from the curing temperature to the normal temperature as illustrated in FIGS. 9A and 9B. Taking this shrinkage into account, the uncured coating resin 3a is required to be applied to the FBG sensor regions and portions of the FBG sensor regions over the protection coating 4 on both sides in the axial direction of the optical fiber 2.

When resin impregnation is to be detected, the resin impregnation detecting system employing the same configuration based on a configuration of a strain detecting system configured to detect a strain of the FBG sensor 5 as illustrated in FIG. 5 is used.

As described above, according to the present invention, there is provided a resin impregnation detection device including: an optical fiber including at least one FBG sensor; and a coating resin, which is coated by applying a compressive strain to the FBG sensor when being cured, in which the coating resin includes a resin to be softened by contact with a detection target resin, and in which the resin impregnation detection device is configured to detect impregnation with the resin by the FBG sensor, which is configured to detect, when the compressive strain applied to the FBG sensor is released during the softening, a change in a Bragg wavelength caused by the release of the compressive strain.

The compressive strain of the coating resin is caused by cure shrinkage of the coating resin or heat shrinkage thereof from a curing temperature to a normal temperature.

Consequently, when the coating resin is softened by the contact with the detection target resin, the compressive strain applied to the FBG sensor is released. Through detection of a change in this strain, it is possible to detect resin impregnation.

The optical fiber includes a plurality of the FBG sensors having different Bragg wavelengths.

The resin impregnation detection device includes the plurality of FBG sensors, and hence can monitor a resin impregnation situation in an axial direction of a coil insulation layer.

The optical fiber includes a protection coating, which coats a portion of the optical fiber other than the FBG sensor, and a diameter of the coating resin is the same or substantially the same as a diameter of the protection coating.

Consequently, the diameter of the coating resin and the diameter of the protection coating are equivalent to each other. Therefore, the resin impregnation detection device can be inserted in any portion as long as the portion is a portion in which the optical fiber can be inserted.

A coating portion of the coating resin is only a half surface of the FBG sensor in a circumferential direction of the FBG sensor.

Consequently, by bending the optical fiber, it is possible to apply the compressive strain to the FBG sensor.

Further, there is provided a coil for a rotating machine including the above-mentioned resin impregnation detection device disposed between a coil conductor of the coil and an insulation tape, which forms a coil insulation layer on an outer side of the coil conductor.

Consequently, by disposing the resin impregnation detection device between the coil conductor and the insulation tape, it is possible to detect resin impregnation in the coil insulation layer.

Further, there is provided a coil for a rotating machine including the above-mentioned resin impregnation detection devices disposed at a plurality of portions between a coil conductor of the coil and an insulation tape, which forms a coil insulation layer on an outer side of the coil conductor, and between layers of the insulation tape.

Consequently, by disposing the resin impregnation detection devices at the plurality of portions, it is possible to monitor the resin impregnation situation in a thickness direction of the coil insulation layer.

Further, there is provided a resin impregnation molding method for a coil for a rotating machine, the resin impregnation molding method including: disposing the above-mentioned resin impregnation detection device at at least one portion, and winding an insulation tape around a coil conductor of the coil, the at least one portion being at least one of a portion between the coil conductor and the insulation tape, which forms a coil insulation layer on an outer side of the coil conductor, and a portion between layers of the insulation tape; and continuing resin impregnation with an impregnated resin until all of the disposed resin impregnation detection devices detect the resin impregnation.

Consequently, by continuing the resin impregnation until all resin impregnation detection devices detect the resin impregnation, it is possible to prevent a failure of the resin impregnation.

The present invention is not limited to each of the above-mentioned embodiments and includes all possible combinations of those embodiments.

INDUSTRIAL APPLICABILITY

The resin impregnation detection device, the coil for a rotating machine, and the resin impregnation molding method for a coil for a rotating machine according to the present invention are applicable to a large number of fields.

REFERENCE SIGNS LIST 1, 1a to 1d resin impregnation detection device, 2 optical fiber, 3, 3a coating resin, 4 protection coating, 5, 5a to 5c FBG sensor, 6 core, 7 clad, 8 optical circulator, 9 ASE light source, 10 optical wavelength meter, 11 coil conductor, 12 insulation tape, 13 impregnated resin, 50 strain detecting system, 100 coil for a rotating machine

The invention claimed is:
1. A resin impregnation detection device, comprising:
an optical fiber including at least one Fiber Bragg Grating (FBG) sensor; and
a coating resin, which is coated by applying a compressive strain to the FBG sensor when being cured, wherein the coating resin includes a resin to be softened by contact with a solvent included in a detection target resin, and wherein the resin impregnation detection device is configured to detect impregnation with the detection target resin by the FBG sensor, which is configured to detect, when the compressive strain applied to the FBG sensor is released during the softening, a change in a Bragg wavelength caused by the release of the compressive strain.

2. The resin impregnation detection device according to claim 1, wherein the compressive strain of the coating resin is caused by cure shrinkage of the coating resin or heat shrinkage of the coating resin from a curing temperature to a normal temperature.

3. The resin impregnation detection device according to claim 2, wherein the optical fiber includes a plurality of FBG sensors having different Bragg wavelengths.

4. The resin impregnation detection device according to claim 2,
wherein the optical fiber includes a protection coating, which coats a portion of the optical fiber other than the FBG sensor, and
wherein a diameter of the coating resin is the same or substantially the same as a diameter of the protection coating.

5. The resin impregnation detection device according to claim 2, wherein a coating portion of the coating resin is only a half surface of the FBG sensor in a circumferential direction of the FBG sensor.

6. The resin impregnation detection device according to claim 1, wherein the optical fiber includes a plurality of FBG sensors having different Bragg wavelengths.

7. The resin impregnation detection device according to claim 6,
wherein the optical fiber includes a protection coating, which coats a portion of the optical fiber other than the FBG sensor, and
wherein a diameter of the coating resin is the same or substantially the same as a diameter of the protection coating.

8. The resin impregnation detection device according to claim 6, wherein a coating portion of the coating resin is only a half surface of the FBG sensor in a circumferential direction of the FBG sensor.

9. The resin impregnation detection device according to claim 1,
wherein the optical fiber includes a protection coating, which coats a portion of the optical fiber other than the FBG sensor, and
wherein a diameter of the coating resin is the same or substantially the same as a diameter of the protection coating.

10. The resin impregnation detection device according to claim 9, wherein a coating portion of the coating resin is only a half surface of the FBG sensor in a circumferential direction of the FBG sensor.

11. The resin impregnation detection device according to claim 1, wherein a coating portion of the coating resin is only a half surface of the FBG sensor in a circumferential direction of the FBG sensor.

12. The resin impregnation detection device according to claim 1, wherein the coating resin coats the FBG sensor, and parts other than the FBG sensor of the optical fiber are coated with a protection coating such that the protection coating is absent over the FBG sensor.

13. A coil for a rotating machine, comprising the resin impregnation detection device of claim 1 disposed between a coil conductor of the coil and an insulation tape, which forms a coil insulation layer on an outer side of the coil conductor.

14. The coil for a rotating machine according to claim 13, wherein the resin impregnation detection devices are disposed at a plurality of portions between the coil conductor of the coil and the insulation tape, and between layers of the insulation tape.

15. A resin impregnation molding method for a coil for a rotating machine, the resin impregnation molding method comprising:
disposing the resin impregnation detection device of claim 1 at at least one portion, and winding an insulation tape around a coil conductor of the coil, the at least one portion being at least one of a portion between the coil conductor and the insulation tape, which forms a coil insulation layer on an outer side of the coil conductor, and a portion between layers of the insulation tape; and
continuing resin impregnation with an impregnated resin until all of the disposed resin impregnation detection devices detect the resin impregnation.

* * * * *